United States Patent [19]

Rishpon et al.

[11] Patent Number: 5,082,550

[45] Date of Patent: Jan. 21, 1992

[54] ENZYME ELECTROCHEMICAL SENSOR ELECTRODE AND METHOD OF MAKING IT

[75] Inventors: Judith Rishpon; Thomas A. Zawodzinski; Shimshon Gottesfeld, all of Los Alamos, N. Mex.

[73] Assignee: The United States of America as represented by the Department of Energy, Washington, D.C.

[21] Appl. No.: 448,475

[22] Filed: Dec. 11, 1989

[51] Int. Cl.$^5$ .............................................. G01N 27/30
[52] U.S. Cl. ........................ 204/403; 204/153.12; 435/182; 435/288; 435/817
[58] Field of Search .................... 204/153.12, 403; 435/817, 182, 288, 291

[56] References Cited

U.S. PATENT DOCUMENTS

| | | |
|---|---|---|
| 4,415,666 | 11/1983 | D'Orazio et al. .................... 435/204 |
| 4,418,148 | 11/1983 | Oberhardt ............................ 435/204 |
| 4,517,291 | 5/1985 | Seago .................................. 435/14 |
| 4,604,182 | 8/1986 | Seago .................................. 204/403 |

FOREIGN PATENT DOCUMENTS 0311377 4/1989 European Pat. Off. .

OTHER PUBLICATIONS

D. Jed Harrison et al., "Characterization of Perfluorosulfonic Acid Polymer Coated Enzyme electrodes and a Miniaturized Integrated Potentiostat for Glucose Analysis in Whole Blood," 60 Anal. Chem., No. 19, pp. 2002–2007 (Oct. 1, 1988).

Primary Examiner—G. L. Kaplan
Attorney, Agent, or Firm—Ray G. Wilson; Paul D. Gaetjens; William R. Moser

[57] ABSTRACT

An electrochemical sensor electrode is formed from an electronic conductor coated with a casting solution containing a perfluorosulfonic acid ionomer and a selected enzyme. The selected enzyme catalyzes a reaction between a predetermined substance in a solution and oxygen to form an electrochemically active compound that is detected at the electronic conductor. The resulting perfluorosulfonic acid polymer provides a stable matrix for the enzyme for long lived enzyme activity, wherein only thin coatings are required on the metal conductor. The polymer also advantageously repels interfering substances from contacting the enzyme and contains quantities of oxygen to maintain a sensing capability during conditions of oxygen depletion in the sample. In one particular embodiment, glucose oxidase is mixed with the perfluorosulfonic acid ionomer to form an electrode for glucose detection.

9 Claims, 3 Drawing Sheets

ENZYME ELECTROCHEMICAL SENSOR ELECTRODE AND METHOD OF MAKING IT

This invention is the result of a contract with the Department of Energy (Contract No. W-7405-ENG-36).

BACKGROUND OF INVENTION

This invention generally relates to enzyme electrochemical sensors and, more particularly, to enzyme electrodes.

Enzyme electrodes are a class of devices that incorporate an enzyme as a catalyzing element on a conventional electrode. The enzyme is placed adjacent the electrode and catalyzes a reaction with a selected substance in which an electroactive species is formed (or consumed) and detected by the electrode to produce a signal functionally related to the amount of the selected substance adjacent the electrode. In potential medical applications of such sensors, small amounts of various substances contained in a body environment can be measured. Such substances may include glucose, urea, uric acid, triglycerides, amino acids, lactic acid, etc. Glucose concentrations are a particularly important indicator of various body conditions, e.g., diabetes, and glucose sensors may be combined with other devices to correct abnormal conditions.

By way of example, the enzyme glucose oxidase catalyzes the reaction of glucose with oxygen to produce gluconic acid and hydrogen peroxide. The presence of the hydrogen peroxide can be detected by an adjacent electrode and the amount of hydrogen peroxide can be determined, whereby the glucose concentration in the material adjacent the enzyme is then known. Conventionally, a selected enzyme is held adjacent the sample material by encapsulating the enzyme between membranes of a polymer suitable for passage of the material to be measured, by including the enzyme in the pore spaces of a suitable membrane, or by forming a membrane which incorporates the enzyme.

U.S. Pat. No. 4,415,666 issued Nov. 15, 1983, to D'Orazio et al., included herein by reference, teaches the use of cellulose acetate and copolymers of cellulose acetate to form a multilayer membrane, incorporating an enzyme in one layer. Numerous disadvantages of the prior art are discussed therein: cellophane membranes can pass interfering high molecular weight substances adjacent the enzyme; thin filter membranes can prevent the passage of interfering materials, but must be too thin to maintain electrode responsiveness to be of practical use; laminated structures require an enzyme adhesive to bond layers together and are subject to delamination; only low enzyme loadings are possible. The sensor taught by the '666 patent attempts to solve these problems by forming a two layer membrane of a cellulose acetate where the glucose oxidase is incorporated within one of the layers to immobilize the enzyme and to allow higher loadings of enzyme to be incorporated within the membrane. An outer layer of a higher density cellulose acetate is formed to contact the sample to preclude passage of interfering materials. The enzyme-containing cellulose acetate layer is formed directly on the high density layer to produce a substantially integral membrane. A membrane thickness of about 1-10 microns for the first layer and about 40-80 microns for the second layer is obtained. The subject membrane is placed in a polarograph having an electrolyte containing oxygen for generating hydrogen peroxide adjacent the cell electrode for sensing. The outer layer is also required to limit the flux of glucose adjacent the enzyme to preclude nonlinear signals arising from oxygen depletion in the membrane.

It would be desirable to provide the enzyme in a thin layer, i.e. less than about 10 microns thick, adjacent the electrode for a rapid response time for glucose concentration changes. The prior art electrodes also require an adjacent source of oxygen to maintain the enzyme reaction and, hence, are sensitive to local oxygen concentrations. It should also be noted that any material forming the sensor must be stable and biocompatible for possible in-vivo use. In addition, it is desirable to minimize interference from other oxidizable substances in a blood environment, such as ascorbic acid and uric acid.

The use of perfluorosulfonic acid polymers, and particularly Nafion (a trademark of Du Pont Company), as a protective membrane for use with glucose oxidase is taught by Harrison et al., "Characterization of Perfluorosulfonic Acid Polymer Coated Enzyme Electrodes and a Miniaturized Integrated Potentiostat for Glucose Analysis in Whole Blood," 60 Anal. Chem., No. 19, pp. 2002-2007 (Oct. 1, 1988), incorporated herein by reference. Enzyme-coated ion-sensitive field effect transistors (ISFET) were coated with Nafion to form a semipermeable membrane over the enzyme layer that reduced the sensitivity to $O_2$ tension and provided satisfactory electrochemical performance, i.e., was semipermeable to glucose, protected the enzyme layer, was biocompatible, and obtained reproducible results. A device having a Nafion layer thickness of 1.7 microns was successfully operated in whole blood sample for about six days before the Nafion layer separated from a glass shroud around the electrode. The 1.7 micron thickness of Nafion provided a signal response at glucose concentrations as low as 1.2 mM. However, a linear response was obtained at glucose concentrations only up to 28 mM and the response time was 5-17 s. Harrison et al. also note problems with adhering the Nafion. Further, any openings in the Nafion cover would expose the enzyme to the material under test, resulting in degradation of the enzyme.

These and other problems of the prior art are addressed by the present invention and an improved enzyme electrochemical sensor is provided.

One object of the present invention is to provide a suitable enzyme adjacent the sensor electrode in a matrix in which the enzyme is not subject to degradation from the material under test.

Another object of the invention is to provide a thin enzyme layer having enhanced response times.

Yet another object is to provide an enzyme in a matrix which precludes interference from undesired oxidizable components in the material to be tested.

One other object of the invention is to provide an electrochemical sensor with a greatly reduced sensitivity to the oxygen tension adjacent the membrane.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention may comprise an electrochemical sensor electrode having an electronic conductor with a thin coating of a persulfonic acid polymer having an enzyme dispersed therein effective to catalyze a reaction between a selected substance and oxygen to generate hydrogen peroxide in said polymer for detection by said conductor. In a particular embodiment, the perfluorosulfonic acid polymer with the dispersed enzyme forms a single coating on said electronic conductor in contact with a solution containing the selected substance.

In another characterization of the present invention, an electrochemical sensor electrode is fabricated from a casting solution containing a perfluorosulfonic acid ionomer and an enzyme selected to determine the concentration of a predetermined substance. The perfluorosulfonic acid ionomer is provided in an alcohol solution which is neutralized to a pH which does not affect the enzyme. The enzyme is then added to the ionomer solution in an amount effective to provide a desired sensitivity for the expected concentration of the predetermined substance. The ionomer solution with the enzyme is then applied to the electronic conductor to form the electrochemical sensor electrode.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION OF THE INVENTION

Figure 1:
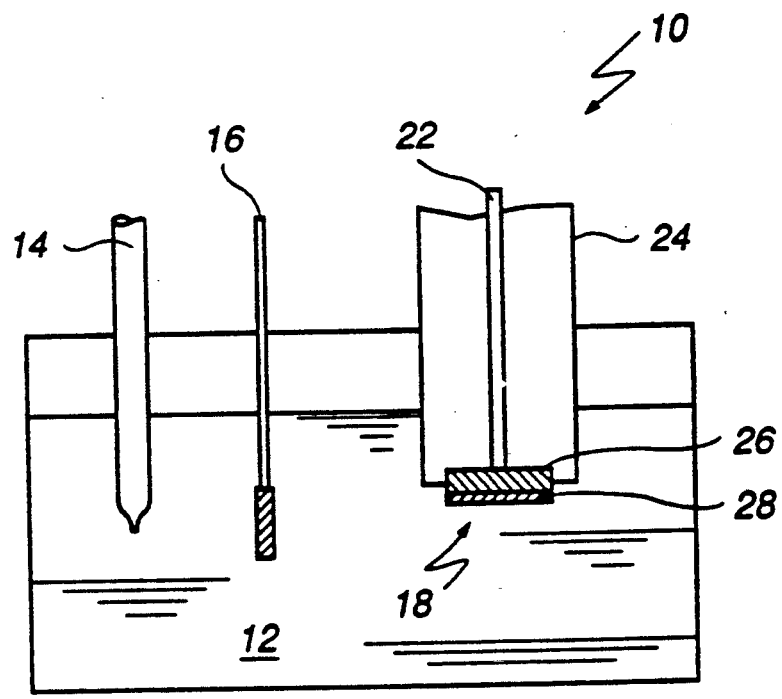
FIG. 1 is a schematic representation of an electrochemical sensor according to the present invention.

In accordance with the present invention, a casting solution of a perfluorosulfonic acid ionomer and an enzyme is prepared and an electrode conductor is coated with the solution to form a film containing the enzyme to a thickness which provides the amount of enzyme needed to obtain a preselected sensitivity with a desired response time to changes in the concentration of a selected material having a reaction with oxygen that is catalyzed by the enzyme. The integrated film can be cast as a membrane or cast directly on an electrode conductor surface without concerns for degrading the enzyme. The perfluorosulfonic acid polymer which is formed provides an insoluble biocompatible matrix for the enzyme and the enzyme is protected against bacterial degradation from an in-vivo or in-vitro environment. Further, the enzyme remains available for continued use in the electrode structure. The perfluorosulfonic acid polymer also dissolves large quantities of oxygen that is then available adjacent the enzyme to promote hydrogen peroxide formation for signal generation.

In a particular embodiment, a glucose sensitive electrode was formed using perfluorosulfonic acid ionomer and glucose oxidase. A perfluorosulfonic acid ionomer, Nafion, is commercially available as a solution in alcohol/water mixtures, typically at 5% by weight of Nafion. The Nafion solution was diluted a substantial amount, e.g., tenfold, by the addition of a phosphate buffer (pH = 7) and glucose oxidase was added to the buffered solution. The resulting solution can then be applied to an electrode by topical application for flat electrodes or by dip coating for meshes and wires. Typical layer thicknesses of 3 microns or less are satisfactory.

As hereinafter shown, the enzyme coating prepared in accordance with the present invention to form an enzyme electrode provides improved performance features over prior art electrochemical sensor electrodes. The electrode is easily fabricated, needing only a single layer of the active Nafion-enzyme material on the electrode conductor. The resulting thin coating provides a rapid response time (2-4 seconds at most) to glucose additions and responds over a wide range of glucose concentrations (at least 1-110 mM) before saturating. The perfluorosulfonate also dissociates in the presence of water in the sample. The resulting negatively charged ions are believed to exclude interfering anions such as ascorbate or ureate. Further, the composite material is extremely stable and exhibits substantial, and nearly constant, performance over a long period of time. The high solubility of oxygen in the Nafion matrix that includes the enzyme catalyst also stabilizes the response and offers potential advantages for electrode use in hypoxic environments or in applications involving high glucose concentrations. The casting mixture (20 $\mu$l) formed according to Example 1., below, was applied to a Pt rotating disc electrode (area = 0.531 cm$^2$) and air dried for about 30 minutes. The resulting coating includes about 4 $\mu$g of enzyme per 100 $\mu$g of Nafion.

EXAMPLE 1

1. Dilute a commercial 5% Nafion solution (Solution Technologies) by a factor of 10 using water.
2. Adjust solution to pH = 7.2 with NaOH and phosphate buffer solution.
3. Add glucose oxidase to the dilute Nafion solution (50 $\mu$l of 10 mg/ml glucose oxidase solution added to 2.5 ml Nafion solution).
4. Apply casting mixture to electrode structure.

It will be appreciated that the perfluorosulfonic acid (Nafion) disassociates in water to form a highly acidic solution that would denature the enzyme. According to the present invention, the enzyme activity is maintained by substantially neutralizing the acidic solution before mixing the enzyme into the perfluorosulfonic acid solution. Once the enzyme is added to form a casting solution, the mixture is promptly applied to the conductive electrode 14, structure and cured to form the composite electrochemical sensor electrode. Surprisingly, the enzyme activity in the composite electrode is then maintained in the perfluorosulfonic acid polymer matrix containing the enzyme.

Referring now to FIG. 1, electrochemical sensor assembly 10 was constructed to incorporate an enzyme electrode according to the present invention. A conventional assembly of electrodes, i.e., reference electrode counter electrode 16, and sensing electrode 18, was placed in a sample solution 12, e.g. glucose solution. Sensing electrode 18 includes signal lead 22 supported by rod 24, which may be Teflon, and connected to metal conductor electrode 26. Enzyme matrix 28, formed according to Example 1., was formed on the surface of metal electrode 26 that faces solution 12 and contacts solution 26 to generate an electroactive material as hereinabove discussed.

The response of sensor electrodes constructed as above was determined for glucose additions to phosphate buffer solutions. The response was determined for a concentration increase of 0.113 M of glucose oxidase in the phosphate buffer. The response time is defined to be the time taken from the point of glucose injection until a higher, steady state current is achieved. This was typically 2-4 seconds for the test sensors having a Nafion-glucose oxidase layer thickness of about 3 microns. A layer thickness of 1-10 microns provides adequate performance. Further, the sensors exhibited stable performance over a test period of over 50 days, as shown in FIG. 1. An initial high level of electrode performance is generally observed for the electrodes followed by a substantially constant performance showing a general maintenance of enzyme activity over the test period.

Figure 2:
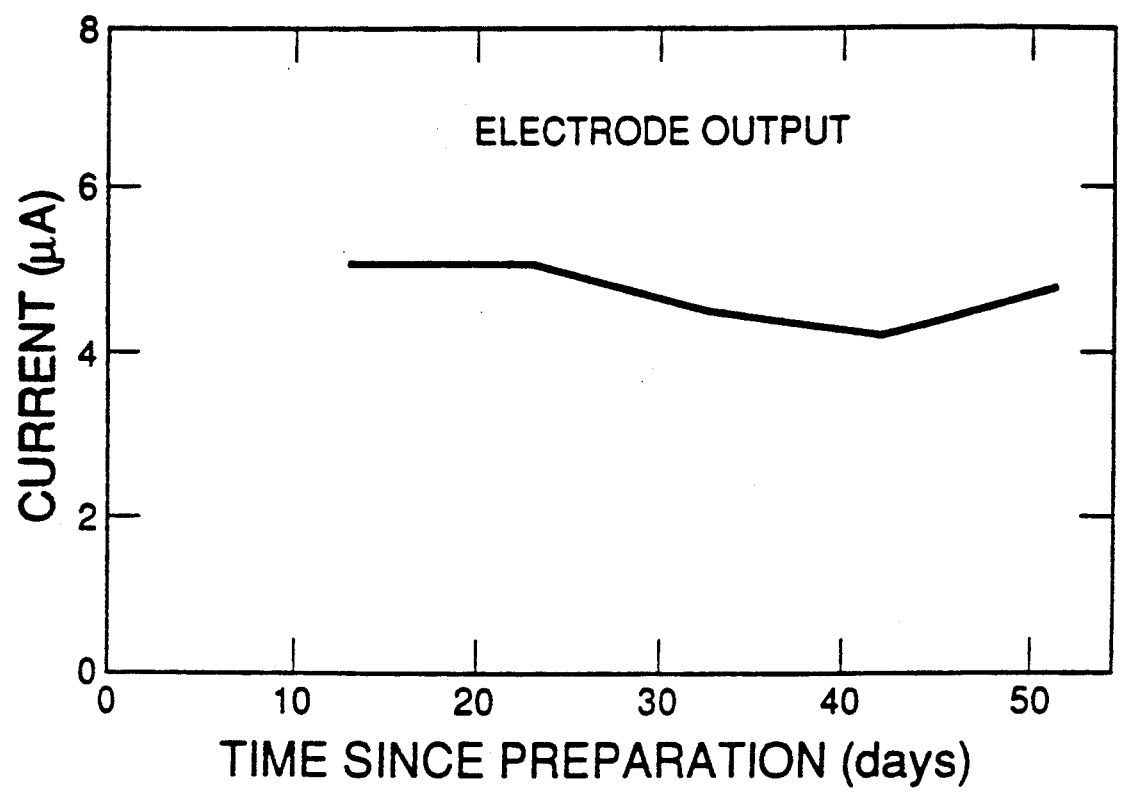
FIG. 2 is a graphical representation showing the output stability of an electrochemical sensor in accordance with the present invention.

FIG. 2 shows a typical response of the enzyme sensor to successive additions of glucose. The current measured at the electrode responds well to stepped increases in glucose concentrations from 1 mM to 113 mM. This range of glucose concentrations is substantially larger than the glucose range achievable with other known glucose sensors, indicating the capability of the perfluorosulfonic acid matrix to maintain an adequate oxygen supply adjacent the enzyme. FIG. 2 also illustrates the response of the electrode to purging of oxygen from the system by bubbling argon gas through a phosphate buffer solution to which glucose had been added. After one hour of treatment, the electrode current was still 40% of the initial value, indicating the effect of oxygen retention in the Nafion and concomitant reduced sensitivity to local oxygen concentrations in the tested medium.

An electrochemical sensor according to the present invention, including a rotating disk electrode conductor, was also tested in human serum samples. The response of the sensor to additions of glucose to the serum was similar to the response measured with phosphate buffer solutions. The addition of 2 mM glucose was readily detected with a response time of 2-4 seconds.

Figure 3:
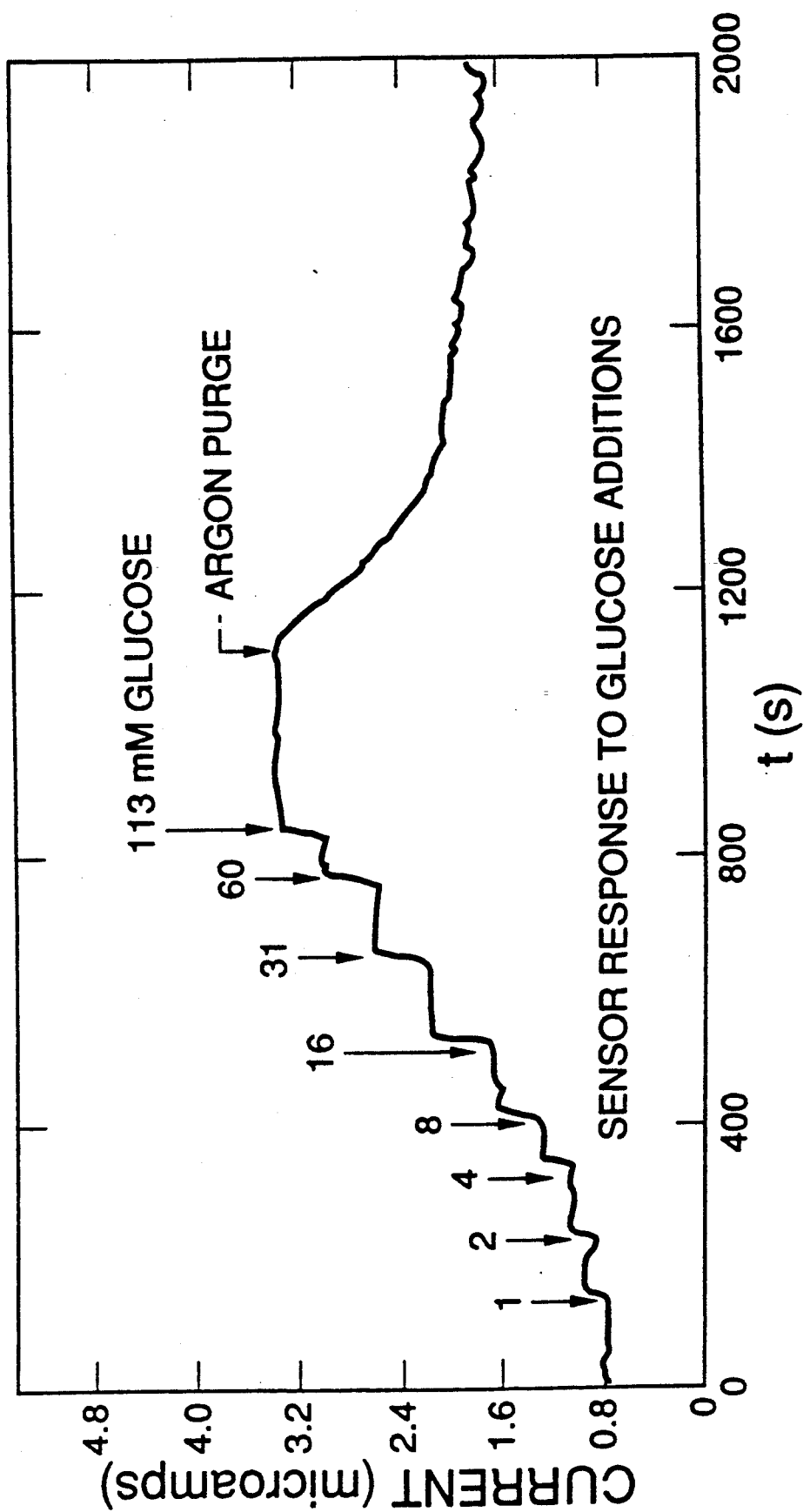
FIG. 3 is a graphical representation of the output response to a range of glucose concentrations of one embodiment of an electrochemical sensor in accordance with the present invention.

While the electrode performance shown in FIGS. 2 and 3 was obtained using sensors formed in accordance with the procedure of Example 1, a wide range of equivalent casting solution mixtures can be used. By way of example, the effect of alcohol content on the sensor activity was determined by replacing various fractions of the phosphate buffer diluent of the 5% Nafion solution with ethanol while maintaining a constant Nafion and enzyme content. Sensors of satisfactory activity were obtained for casting solutions containing up to 40% alcohol by weight, although a limiting concentration of alcohol has not been determined.

Enzyme loadings of 4, 20, and 100 mg glucose oxidase per gram Nafion were found to respond adequately to glucose changes. Table A illustrates the sensor's response to 16 mM glucose in solution. It can be seen that the sensor sensitivity (current/loading ratio) is relatively constant.

TABLE A

| mg glucose oxidase/g Nafion | Current ($\mu$) | Sensitivity |
| --- | --- | --- |
| 4 | 0.70 | 0.175 |
| 20 | 4.0 | 0.20 |
| 100 | 19.8 | 0.198 |

A protective layer of Nafion without glucose oxidase was added to the electrochemical sensor electrode structure in order to determine the effect on the enzyme film performance. Although there was no observed effect on the electrochemical sensor electrode response time from the Nafion layer, there was a decrease of about 75% in the sensor activity. The protective Nafion film was about 1 $\mu$m thick over the 1 $\mu$m thick enzyme film.

It will also be appreciated that the present invention is not limited to use with the enzyme glucose oxidase. Many other enzymes react with specific substances to produce hydrogen peroxide for generating an electrical signal functionally related to the presence of such specific substances. Suitable enzymes include galactose oxidase, alcohol oxidase, lactic acid oxidase, amino acid oxidase, and cholosterol oxidase. The relative equivalence of these enzymes for use in electrochemical sensors is shown in U.S. Pat. No. 4,795,707, issued Jan. 3, 1989, to Niiyama et al., incorporated herein by reference. Such enzymes which produce hydrogen peroxide in the presence of a specific substance may be incorporated in a perfluorosulfonic acid polymer in accordance with the present invention to form a stable, sensitive electrochemical sensor electrode.

The foregoing description of various embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An electrochemical sensor electrode, comprising:
an electronic conductor, and
a thin coating on said conductor of a perfluorosulfonic acid polymer having an enzyme dispersed therein effective to catalyze a reaction between a selected substance and oxygen to generate hydrogen peroxide in said polymer for detection at said conductor.

2. An electrochemical sensor electrode according to claim 1, wherein said enzyme is selected from the group consisting of glucose oxidase, galactose oxidase, alcohol oxidase, lactic acid oxidase, amino acid oxidase, and cholesterol oxidase.

3. An electrochemical sensor electrode according to claim 1, wherein said coating is 1-10 microns in thickness.

4. An electrochemical sensor electrode, consisting essentially of:
an electronic conductor, and
a thin coating on said conductor of a perfluorosulfonic acid polymer having an enzyme dispersed therein effective to catalyze a reaction between a selected substance and oxygen to generate hydrogen peroxide in said polymer for detection at said conductor.

5. An electrochemical sensor electrode according to claim 4, wherein said enzyme is selected from the group consisting of glucose oxidase, galactose oxidase, alcohol oxidase, lactic acid oxidase, amino acid oxidase, and cholesterol oxidase.

6. A method of making an electrochemical sensor electrode using a selected enzyme to determine the concentration of a predetermined substance, comprising the steps of:

providing an electronic conductor;

providing a perfluorosulfonic acid ionomer in an alcohol solution;

neutralizing said solution to form a pH which does not affect said enzyme;

adding said enzyme to said ionomer solution in an amount effective to provide a desired sensitivity for said concentration of said predetermined substance; and applying said ionomer solution with said enzyme to said conductor.

7. A method according to claim 6, wherein said enzyme is selected from the group consisting of glucose oxidase, galactose oxidase, alcohol oxidase, lactic acid oxidase, amino acid oxidase, and cholesterol oxidase.

8. A method according to claim 7, wherein said enzyme is glucose oxidase and said effective amount is 4–100 mg glucose oxidase/g perflurosulfonic acid ionomer.

9. A method according to claim 6, wherein said ionomer solution with said enzyme is applied to form a coating of 1–10 microns in thickness on said conductor.

* * * * *